(12) United States Patent
Rezai et al.

(10) Patent No.: US 12,343,160 B2
(45) Date of Patent: Jul. 1, 2025

(54) EVALUATING PAIN OF A USER VIA TIME SERIES OF PARAMETERS FROM PORTABLE MONITORING DEVICES

(71) Applicant: West Virginia University Board of Governors on behalf of West Virginia University, Morgantown, WV (US)

(72) Inventors: Ali Rezai, Morgantown, WV (US); Victor Finomore, Morgantown, WV (US)

(73) Assignee: WEST VIRGINIA UNIVERSITY BOARD OF GOVERNORS ON BEHALF OF WEST VIRGINIA UNIVERSITY, Morgantown, WV (US)

( * ) Notice: Subject to any disclaimer, the term of this patent is extended or adjusted under 35 U.S.C. 154(b) by 0 days.

(21) Appl. No.: 17/927,395

(22) PCT Filed: Jun. 1, 2021

(86) PCT No.: PCT/US2021/035267
§ 371 (c)(1),
(2) Date: Nov. 23, 2022

(87) PCT Pub. No.: WO2021/243336
PCT Pub. Date: Dec. 2, 2021

(65) Prior Publication Data
US 2023/0277122 A1 Sep. 7, 2023

Related U.S. Application Data
(60) Provisional application No. 63/032,095, filed on May 29, 2020.

(51) Int. Cl.
*A61B 5/00* (2006.01)
*A61B 5/11* (2006.01)
*A61B 5/16* (2006.01)

(52) U.S. Cl.
CPC .......... *A61B 5/4824* (2013.01); *A61B 5/1118* (2013.01); *A61B 5/165* (2013.01);
(Continued)

(58) Field of Classification Search
CPC .......... G09B 7/00; G09B 7/02; A61B 5/4824; A61B 5/4827
See application file for complete search history.

(56) References Cited

U.S. PATENT DOCUMENTS 9,782,122 B1 * 10/2017 Pulliam ................ A61B 5/4839
2002/0128866 A1 * 9/2002 Goetzke ................ G16H 50/50
705/2

(Continued)

FOREIGN PATENT DOCUMENTS

CN 107209807 A 9/2017
CN 107392109 A 11/2017
(Continued)

OTHER PUBLICATIONS

Lee, Jeungchan, et al. "Machine learning-based prediction of clinical pain using multimodal neuroimaging and autonomic metrics." Pain 160.3 (2019): 550.
(Continued)

*Primary Examiner* — Peter R Egloff
(74) *Attorney, Agent, or Firm* — Tarolli, Sundheim, Covell & Tummino LLP (57) ABSTRACT

Systems and methods are provided for evaluating pain for a user. A first pain-relevant parameter representing the user is monitored at an in-vivo sensing device over a defined period to produce a time series for the first pain-relevant parameter. A value for a second pain-relevant parameter for the user is obtained at first and second times in the defined period from the user via a portable computing device to provide respective first and second values for the second pain-relevant
(Continued)

parameter. A value is assigned to the user via a predictive model according to the time series for the first pain-relevant parameter, the first value for the second pain-relevant parameter, and the second value for the second pain-relevant parameter.

20 Claims, 6 Drawing Sheets

(52) U.S. Cl.
CPC .......... *A61B 5/4815* (2013.01); *A61B 5/7264* (2013.01); *A61B 5/7275* (2013.01); *A61B 5/7475* (2013.01); *A61B 5/6802* (2013.01)

(56) References Cited

U.S. PATENT DOCUMENTS

| | | | |
|---|---|---|---|
| 2003/0144829 A1 | 7/2003 | Geatz et al. | |
| 2011/0087125 A1* | 4/2011 | Causevic | A61B 5/24 |
| | | | 600/544 |
| 2012/0123232 A1 | 5/2012 | Najarian et al. | |
| 2012/0130196 A1 | 5/2012 | Jain et al. | |
| 2015/0133812 A1* | 5/2015 | deCharms | A61B 5/165 |
| | | | 600/559 |
| 2016/0063205 A1 | 3/2016 | Moturu et al. | |
| 2016/0235324 A1* | 8/2016 | Mershin | A61B 5/6803 |
| 2018/0008191 A1 | 1/2018 | Cronin et al. | |
| 2018/0103851 A1 | 4/2018 | Tzvieli | |
| 2020/0364566 A1* | 11/2020 | Banisakher | G16H 50/30 |

FOREIGN PATENT DOCUMENTS

| | | |
|---|---|---|
| WO | 2018/063637 A1 | 4/2018 |
| WO | 2019/136246 A1 | 7/2019 |

OTHER PUBLICATIONS

PCT Search Report for corresponding international Application Serial No. PCT/US2021/035267, mailed Oct. 14, 2021, pp. 1-2.
Australian Government Examination report No. 1, dated Nov. 21, 2023 for corresponding Application No. 2021280365, pp. 1-4.
Fan Yang, "Continuous Pain Assessment Using Ensemble Feature Selection from Wearable Sensor Data", 2019 IEEE International Conference on Bioinformatics and Biomedicine (BIBM), IEEE, Nov. 18, 2019, pp. 569-576, XP033704116, DOI: 10.1109/BIBM47256.2019.8983282.
International Search Report dated Jun. 20, 2024 for corresponding application 21814241.2-1113/41570170 PCT/US2021035267, 8 pages.
Corresponding Chinese Patent Application No. 202180039001.5, First Office Action, dated Dec. 20, 2024.

* cited by examiner

EVALUATING PAIN OF A USER VIA TIME SERIES OF PARAMETERS FROM PORTABLE MONITORING DEVICES

RELATED APPLICATIONS

This application is a U.S. National Stage Application filed under 35 USC 371, claiming priority to Serial No. PCT/US2021/035267, filed on 1 Jun. 2021; which claims priority from U.S. Provisional Patent Application Ser. No. 63/032,095, filed 29 May 2020, the entireties of which are hereby incorporated herein by reference.

TECHNICAL FIELD

This invention relates to an evaluation of pain of a user via time series of parameters received from portable monitoring devices.

BACKGROUND

Measuring pain experienced by a subject is difficult, and is currently limited, for the most part, to observation of the subject's behavior and self-reporting. However, since both observation and self-reporting are subjective, making an objective measure of experienced pain or an increase in pain by itself, in response to a stimulus, or effectiveness of various treatments difficult to measure. Unfortunately, a number of disorders present with chronic pain and pain as an important feature of the condition, and therefore, the inability of caregivers to objectively measure the subject's pain levels, and in particular, a change in pain level, can complicate diagnosis and management of these conditions and disorders.

SUMMARY

In accordance with one aspect of the invention, a method is provided for evaluating pain for a user. A first pain-relevant parameter representing the user is monitored at an in-vivo sensing device over a defined period to produce a time series for the first pain-relevant parameter. A value for a second pain-relevant parameter for the user is obtained at first and second times in the defined period from the user via a portable computing device to provide respective first and second values for the second pain-relevant parameter. A value is assigned to the user via a predictive model according to the time series for the first pain-relevant parameter, the first value for the second pain-relevant parameter, and the second value for the second pain-relevant parameter.

In accordance with another aspect of the invention, a system is provided for evaluating pain for a user. The system includes an in-vivo sensing device that monitors a first pain-relevant parameter representing the user over a defined period to produce a time series for the first pain-relevant parameter. A portable computing device obtains a value for a second pain-relevant parameter for the user at first and second times in the defined period to provide respective first and second values for the second pain-relevant parameter. A predictive model assigns a value to the user according to the time series for the first pain-relevant parameter, the first value for the second pain-relevant parameter, and the second value for the second pain-relevant parameter.

In accordance with a further aspect of the invention, a system is provided for evaluating pain for a user. The system includes a wearable device that monitors a first pain-relevant parameter representing the user over a defined period to produce a time series for the first pain-relevant parameter. The first pain-relevant parameter is a motor parameter or a physiological parameter. A portable computing device obtains a value for a second pain-relevant parameter for the user at first and second times in the defined period to provide respective first and second values for the second pain-relevant parameter. The second pain-relevant parameter is either a cognitive parameter, a sleep parameter, or a psychosocial parameter, and is determined from an input of the user via a user interface of the mobile device. A predictive model assigns a value to the user according to the time series for the first pain-relevant parameter, the first value for the second pain-relevant parameter, and the second value for the second pain-relevant parameter.

DETAILED DESCRIPTION

A "pain-relevant parameter" is a physiological, cognitive, sensory, sleep, motor, genetic, psychosocial, or behavioral parameter that is relevant to detecting or predicting pain for a user.

A "biological rhythm" is any chronobiological phenomenon that affects human beings, including but not limited to, circadian rhythms, ultradian rhythms, infradian rhythms, diurnal cycle, sleep/wake cycles, and patterns of life.

A "portable monitoring device," as used herein, refers to a device that is worn by, carried by, or implanted within a user that incorporates either or both of an input device and user interface for receiving input from the user and sensors for monitoring either a pain-relevant parameter or a parameter that can be used to calculate or estimate a pain-relevant parameter.

An "index", as used herein, is intended to cover composite statistics derived from a series of observations and used as an indicator or measure. An index can be an ordinal, continuous, or categorical value representing the observations and correlations, and should be read to encompass statistics traditionally referred to as "scores" as well as the more technical meaning of index.

An "in-vivo sensing device," as used herein, is an implanted, ingested, or wearable device used to measure a pain-relevant parameter.

A "portable computing device," as used herein, is a computing device that can carried by the user, such as a smartphone, smart watch, tablet, notebook, and laptop, that can measure a pain-relevant parameter either through sensors on the device or via interaction with the user. A portable computing device can include, for example, a user interface for receiving an input from the user, kinematic sensors for measuring activity by the user, and location services that track a location of the user.

As used herein, a "predictive model" is a mathematical model or machine learning model that either predicts a future state of a parameter or estimates a current state of a parameter that cannot be directly measured.

Figure 1:
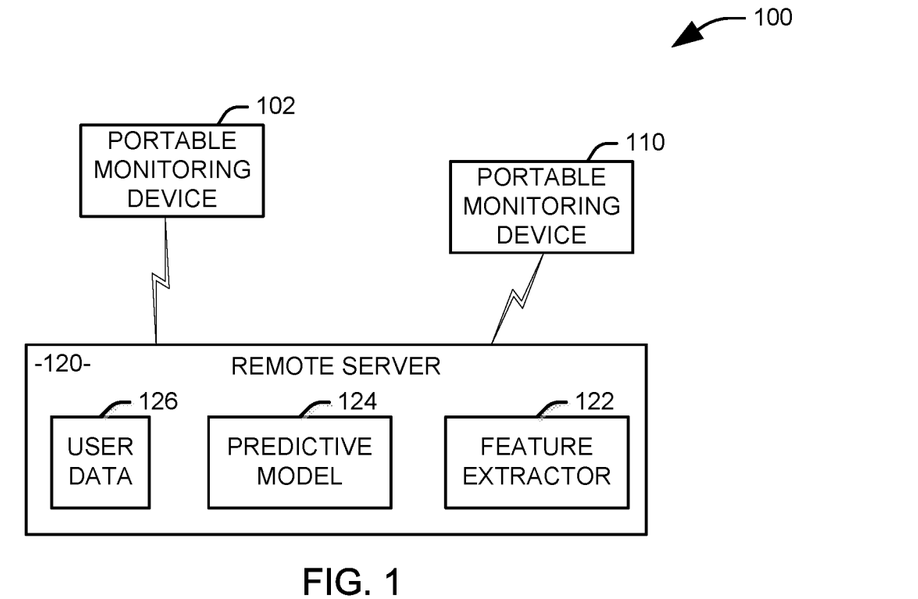
FIG. 1 illustrates a system for evaluating pain of a user in accordance with an aspect of the present invention.

FIG. 1 illustrates a system 100 for evaluating pain for a user in accordance with an aspect of the present invention. In one implementation, the system 100 can be used to monitor the pain level of an individual experiencing chronic pain. The system 100 includes a plurality of portable monitoring devices 102 and 110 that include sensors for monitoring systems tracking pain-relevant parameters for the user. It will be appreciated that a given portable monitoring device (e.g., 102) can either communicate directly with a remote server 120 to provide the pain-relevant parameters to the server or with another portable monitoring device (e.g., 110) that relays the pain-relevant parameters to the server. In one example, the plurality of portable monitoring devices can include an in-vivo sensing device and a portable computing device. By using portable monitoring devices 102 and 110, measurements can be made continuous from any of a user's home, classroom, job, or sports field—literally anywhere from the battlefield to the board room. As noted above, pain-relevant parameters can include at least physiological, cognitive, motor/musculoskeletal, sensory, sleep, biomarkers and behavioral parameters. Table I provides non-limiting examples of physiological parameters that can be measured and exemplary tests, devices, and methods, to measure the physiological parameters.

TABLE I

| Physiological Parameter | Exemplary Devices and Methods to Measure Physiological Parameters |
|---|---|
| Brain Activity | Electroencephalogram, Magnetic Resonance Imaging, including functional Magnetic Resonance Imaging (fMRI), PET, SPECT, MEG, near-infrared spectroscopy, functional near-infrared spectroscopy, and other brain imaging modalities looking at electrical, blood flow, neurotransmitter, and metabolic function |
| Heart rate | Electrocardiogram and Photoplethysmogram |
| Heart rate variability | Electrocardiogram, Photoplethysmogram |
| Eye tracking | Pupillometry, including tracking saccades, fixations, and pupil size (e.g., dilation) |
| Perspiration | Perspiration sensor |
| Blood pressure | Sphygmomanometer |
| Body temperature | Thermometer, infrared thermography |
| Blood oxygen saturation and respiratory rate | Pulse oximeter/accelerometer |
| Skin conductivity | Electrodermal activity |
| Facial emotions | Camera or EMG based sensors for emotion and pain |
| Sympathetic and parasympathetic tone | Derived from the above measurements |

The physiological parameters can be measured via wearable or implantable devices as well as self-reporting by the user via applications in a mobile device, which facilitates measuring these physiological parameters in a naturalistic, non-clinical setting. For example, a smart watch, ring, or patch can be used to measure the user's heart rate, heart rate variability, body temperature, blood oxygen saturation, movement, and sleep. These values can also be subject to a diurnal analysis to estimate variability and reviewed in view of expected changes due to biological rhythms, as well as deviations from an expected pattern of biological rhythms. For example, the biological rhythms of a user can be tracked for a predetermined period (e.g., ten days), to establish a normal pattern of biological rhythms. Oscillations in biological rhythms can be detected as departures from this established pattern. II provides non-limiting examples of cognitive parameters that are gamified and that can be measured and exemplary methods and tests/tasks to measure such cognitive parameters. The cognitive parameters can be assessed by a battery of cognitive tests that measure, for example, executive function, decision making, working memory, attention, and fatigue.

TABLE II

| Cognitive Parameter | Exemplary Tests and Methods to Measure Cognitive Parameters |
|---|---|
| Temporal discounting | Kirby Delay Discounting Task |
| Alertness and fatigue | Psychomotor Vigilance Task |
| Focused attention and response inhibition | Erikson Flanker Task |
| Working memory | N-Back Task |
| Attentional bias towards emotional cues | Dot-Probe Task |
| Inflexible persistence | Wisconsin Card Sorting Task |
| Decision making | Iowa Gambling Task |
| Risk taking behavior | Balloon Analogue Risk Task |
| Inhibitory control | Anti-Saccade Task |
| Sustained attention | Sustained Attention |
| Executive function | Task Shifting or Set Shifting Task |

These cognitive tests can be administered in a clinical/laboratory setting or in a naturalistic, non-clinical setting such as when the user is at home, work or other non-clinical setting. A smart device, such as a smartphone, tablet, or smart watch, can facilitate measuring these cognitive parameters in a naturalistic, non-clinical setting. For example, the Erikson Flanker, N-Back and Psychomotor Vigilance Tasks can be taken via an application on a smart phone, tablet, or smart watch.

TABLE III provides non-limiting examples of parameters associated with movement and activity of the user, referred to herein alternatively for ease of reference as "motor parameters," that can be measured and exemplary tests, devices, and methods. The use of portable monitoring, in-vivo sensing, and portable computing devices allows the motor parameters to be measured. Using embedded accelerometer, GPS, and cameras, the user's movements can be captured and quantified to see how pain affects them and related to the pain-relevant parameters.

TABLE III

| Motor/Musculoskeletal Parameter | Exemplary Tests and Methods to Measure Motor/Musculoskeletal Parameters |
|---|---|
| Activity level | Daily movement total, time of activities, from wearable accelerometer, steps, Motion Capture data, gait analysis, GPS, force plates |
| Gait analysis | Gait mat, camera, force plats |
| Range of motion | Motion capture, camera, |

TABLE IV provides non-limiting examples of parameters associated with sensory acuity of the user, referred to herein alternatively for ease of reference as "sensory parameters," that can be measured and exemplary tests, devices, and methods.

TABLE IV

| Sensory Parameter | Exemplary Tests and Methods to Measure sensory Parameters |
|---|---|
| Vision | Visual acuity test, visual field tests, eye tracking, EMG |
| Hearing | Hearing tests |
| Touch | Two-point discrimination, frey filament |
| Smell/taste | |
| Vestibular | Vestibula function test |

TABLE V provides non-limiting examples of parameters associated with a sleep quantity and quality of the user, referred to herein alternatively for ease of reference as "sleep parameters," that can be measured and exemplary tests, devices, and methods.

TABLE V

| Sleep Parameter | Exemplary Tests and Methods to Measure Sleep Parameters |
|---|---|
| Sleep from wearables | Sleep onset & offset, sleep quality, sleep quantity, from wearable accelerometer, temperature, and PPG, |
| Sleep Questions | Pittsburg Sleep Quality Index, Functional Outcomes of Sleep Questionnaire, Fatigue Severity Scale, Epworth Sleepiness Scale |
| Devices | Polysomnography; ultrasound, camera, bed sensors |
| Circadian Rhythm | Light sensors, actigraphy, serum levels, core body temperature |

TABLE VI provides non-limiting examples of parameters extracted by locating biomarkers associates with the user, referred to herein alternatively for ease of reference as "biomarker parameters," that can be measured and exemplary tests, devices, and methods. Biomarkers can also include imaging and physiological biomarkers related to a state of chronic pain and improvement or worsening of the chronic pain state.

TABLE VI

| Biomarkers Parameter | Exemplary Tests and Methods to Measure Biomarkers Parameters |
|---|---|
| Genetic biomarkers | Genetic testing |
| Immune biomarkers including TNF-alpha, immune alteration (e.g., ILs), oxidative stress, and hormones (e.g., cortisol) | Blood, saliva, and/or urine tests |

Table VII provides non-limiting examples of psychosocial and behavioral parameters, referred to herein alternatively for ease of reference as "psychosocial parameters," that can be measured and exemplary tests, devices, and methods.

TABLE VII

| Psychosocial or Behavioral Parameter | Exemplary Tests and Methods to Measure Psychosocial or Behavioral Parameters |
|---|---|
| Symptom log | Presence of specific symptoms (i.e., fever, headache, cough, loss of smell) |
| Medical Records | Medical history, prescriptions, setting for treatment devices such as spinal cord stimulator, imaging data |
| Pain Rating | Visual Analog Scale, Defense & Veterans pain rating scale, pain scale, Pain Assessment screening tool and outcomes registry |
| Burnout | Burnout inventory or similar |

TABLE VII-continued

| Psychosocial or Behavioral Parameter | Exemplary Tests and Methods to Measure Psychosocial or Behavioral Parameters |
|---|---|
| Physical, Mental, and Social Health | User-Reported Outcomes Measurement Information System (PROMIS), Quality of Life Questionnaire |
| Depression | Hamilton Depression Rating Scale |
| Anxiety | Hamilton Anxiety Rating Scale |
| Mania | Snaith-Hamilton Pleasure Scale |
| Mood/ Catastrophizing scale | Profile of Mood States; Positive Affect Negative Affect Schedule |
| Affect | Positive Affect Negative Affect Schedule |
| Impulsivity | Barratt Impulsiveness Scale |
| Adverse Childhood Experiences | Childhood trauma |
| Daily Activities | Exposure, risk taking |
| Daily Workload and Stress | NASA Task Load Index, Perceived Stress Scale (PSS), Social Readjustment Rating Scale (SRRS) |
| Social Determents of Health | Social determents of health questionnaire |

The behavioral and psychosocial parameters can measure the user's functionality as well as subjective/self-reporting questionnaires. The subjective/self-reporting questionnaires can be collected in a clinical/laboratory setting or in a naturalistic, in the wild, non-clinical setting such as when the user is at home, work, or other non-clinical setting. A smart device, such as a smartphone, tablet, or personal computer can be used to administer the subjective/self-reporting questionnaires. Using embedded accelerometers and cameras, these smart devices can also be used to capture the facial expression analysis to analyze the user's facial expressions that could indicate mood, anxiety, depression, agitation, and fatigue.

In addition to one or more combinations of physiological, cognitive, motor/musculoskeletal, sensory, sleep, biomarkers, and behavioral parameters, clinical data can also be part of the multi-dimensional feedback approach to evaluating pain. Such clinical data can include, for example, the user's clinical state, the user's medical history (including family history), employment information, and residential status.

The remote server that analyzes the data collected by the portable monitoring devices 102 and 110. The remote server 120 can be implemented as a dedicated physical server or as part of a cloud server arrangement. In addition to the remote server, data can be analyzed on the local device itself and/or in a federated learning mechanism. Information received from the portable monitoring devices 102 and 110 is provided to a feature extractor 122 that extracts a plurality of features for use at a predictive model 124. The feature extractor 122 determines categorical and continuous parameters representing the pain-relevant parameters. In one example, the parameters can include descriptive statistics, such as measures of central tendency (e.g., median, mode, arithmetic mean, or geometric mean) and measures of deviation (e.g., range, interquartile range, variance, standard deviation, etc.) of time series of the monitored parameters, as well as the time series themselves. Specifically, the feature set provided to the predictive model will include, for at least one parameter, either two values representing the value for the parameter at different times or a single value, such as a measure of central tendency or a measure of deviation which represents values for the parameter across a plurality of times.

In other examples, the features can represent departures of the patient from an established pattern for the features. For example, values of a given parameter can be tracked over-time, and measures of central tendency can be established, either overall or for particular time periods. The collected features can represent a departure of a given parameter from the measure of central tendency. For example, changes in the activity level of the user, measured by either or both of kinematic sensors and global positioning system (GPS) tracking can be used as a pain-relevant parameter. Additional elements of monitoring can include the monitoring of the user's compliance with the use of a smart phone, TV, portable device, a portable device. For example, a user may be sent messages by the system inquiring on their pain level, general mood, or the status of any other pain-relevant parameter on the portable computing device. A measure of compliance can be determined according to the percentage of these messages to which the user responds via the user interface on the portable computing device.

In one implementation, the feature extractor 122 can perform a wavelet transform on a time series of values for one or more parameters to provide a set of wavelet coefficients. It will be appreciated that the wavelet transform used herein is two-dimensional, such that the coefficients can be envisioned as a two-dimensional array across time and either frequency or scale.

For a given time series of parameters, $x_i$, the wavelet coefficients, $W_a(n)$, produced in a wavelet decomposition can be defined as:

$$W_a(n) = a^{-1} \sum_{i=1}^{M} x_i \psi\left(\frac{i-n}{a}\right) \qquad \text{Eq. 3}$$

wherein $\psi$ is the wavelet function, M is the length of the time series, and a and n define the coefficient computation locations.

The feature extractor 122 can also include a facial expression classifier (not shown) that evaluates recorded data from a camera and/or recorded images or videos of the patient's face from one of the portable monitoring devices 102 and 110, such as a smartphone or other mobile device, to assign an emotional state to the user at various times throughout the day. The extracted features can be categorical, representing the most likely emotional state of the patient, or continuous, for example, as a time series of probability values for various emotional states (e.g., anxiety, discomfort, anger, etc.) as determined by the facial expression classifier. It will be appreciated that the facial expression classifier can be implemented using one or more of the models discussed below for use in the predictive model 124.

The predictive model 124 can also utilize user data 126 stored at the remote server 120, including, for example, employment information (e.g., title, department, shift), age, sex, home zip code, genomic data, nutritional information, medication intake, household information (e.g., type of home, number and age of residents), social and psychosocial data, consumer spending and profiles, financial data, food safety information, the presence or absence of physical abuse, and relevant medical history. In addition, the model can combine multiple users to interact together to refine the prediction, such as a social model of spouse, children, family, co-workers, friends and others.

The predictive model 124 can utilize one or more pattern recognition algorithms, each of which analyze the extracted features or a subset of the extracted features to assign a continuous or categorical parameter to the user. In one example, the predictive model 124 can assign a continuous parameter that corresponds to a value for a pain scale, such as the Oswestry Disability Index, the Numerical Rating Scale, or the Mankoski Pain Scale. The continuous parameter provided by the predictive model 124 correlates with physiological measures and can be used as a surrogate metric for any of these pain scales or other subjective measures of pain. Alternatively, the predictive model 124 can assign a categorical parameter that corresponds to a category associated with a pain scale, such as the Wong-Baker Faces Pain Scale and the Color Analog Scale. The predictive model 124 can either determine a value for a current pain level of the patient or predict a pain value for the patient at some point in the future. In one example, the computed index can be compared with self-reported pain and mood of the user to identify pain catastrophization. In addition, values for pain levels for a patient or subject can be used to quantify a placebo effect during treatment or clinical trials by comparing self-reported pain levels, for example, via a numerical pain scale, to the objective pain value produced by the predictive model 124. The generated parameter can be stored in a non-transitory computer readable medium, for example, as part of a record in an electronic health records database, or used to guide immediate treatment, for example, via a therapeutic device implanted in, worn by, or carried by the user.

Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. The training process can be accomplished on a remote system and/or on the local device or wearable, app. The training process can be achieved in a federated or non-federated fashion. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines, regression models, self-organized maps, fuzzy logic systems, data fusion processes, boosting and bagging methods, rule-based systems, or artificial neural networks.

Federated learning (aka collaborative learning) is a predictive technique that trains an algorithm across multiple decentralized edge devices or servers holding local data samples, without exchanging their data samples. This approach stands in contrast to traditional centralized predictive techniques where all data samples are uploaded to one server, as well as to more classical decentralized approaches which assume that local data samples are identically distributed. Federated learning enables multiple actors to build a common, robust predictive model without sharing data, thus addressing critical issues such as data privacy, data security, data access rights, and access to heterogeneous data. Its applications are spread over a number of industries including defense, telecommunications, IoT, or pharmaceutics.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier. Another example is utilizing an autoencoder to detect outlier in pain-relevant parameters as an anomaly detector to identify when various parameters are outside their normal range for an individual due to an increase or decrease in pain.

Many ANN classifiers are fully connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

In one implementation, the predictive model 124 can include a constituent model that predicts future values for pain-related parameters, such as a convolutional neural network that is provided with one or more two-dimensional arrays of wavelet transform coefficients as an input. The wavelet coefficients detect changes not only in time, but also in temporal patterns, and can thus reflect changes in the ordinary biological rhythms of the user. In one implementation, the pain-related parameters predicted by the constituent models can include measured parameters such as heart rate and heart rate variability as well as symptoms such as sleep disruption and reduced activity. It will be appreciated that a given constituent model can use data in addition to the wavelet coefficients, such as other extracted features and user data 126 to provide these predictions.

Additionally, or alternatively, the predictive model can use constituent models that predict current or future values for metrics of overall wellness, with these measures then used as features for generating the output of the predictive model. For example, these metrics can include values representing fatigue, physical stress, emotional stress, sleep disruption, work load, stress load, and additive behavior. By using these values for identifying or predicting increases in the pain level of the user, triggers for these increases can be identified and used for more effective treatment of pain. Conversely, where the user's pain decreases, these values can be evaluated to associate the improvement or stability with the change in these parameters. This data can also be used to group the patient with patients who respond similarly to these parameters, with data fed back from patients within a given group used to better tailor the model to the patient. The model can also be used to facilitate a feedback strategy to the subject, participant, health care provider, care team, and other entities to facilitate the diagnosis of chronic pain, management of pain, return to work and function, and to improve the response to therapies for pain including medications, lesioning, and other procedures such as neuromodulation including neurostimulation, spinal cord stimulation, infusion and other approaches.

The output of the predictive model 124 can be a categorical parameter representing a status of the user, such as a category on a pain scale or a state of pain catastrophization, or ranges of likelihoods for a current or predicted status. In another implementation, the output of the predictive model 124 can be a continuous parameter, such as a likelihood of a predicted or current status or a value representing current pain levels. In one example, the predictive model 124 can include one or more constituent models that predict a value for a pain-related parameter at a future time. For example, a given model can predict a heart rate or heart rate variability for a user at a future time (e.g., in three days) based on received data from the feature extractor 122 and stored user data 126. These predicted values can be provided to a user or utilized as inputs to additional models to predict a status of the user at the future time. In one example, the predictive model 124 includes a plurality of convolutional neural networks, each configured to predict a future value for a pain-related parameter, with the predicted values from the plurality of convolutional neural networks being used to predict a future status (e.g., pain level, activity level, or sleep quality) of the user.

In some implementations, the predictive model 124 can include a feedback component 128 can tune various parameters of the predictive model 124 based upon the accuracy of predictions made by the model. In one example, the feedback component 128 can be shared by a plurality of predictive models 124, with the outcomes for users associated with each predictive model compared to the outcomes predicted by the output of the model. Parameters associated with the model, such as thresholds for producing categorical inputs or outputs from continuous values, can be adjusted according to the differences in the actual and predicted outcomes. In one example, a continuous output of the system can be compared to a threshold value to determine if the patient is increase or decrease in pain related parameters. This threshold can be varied by the feedback model 128 to increase the accuracy of the determination.

Alternatively, the predictive model 124 can obtain feedback at the level of the individual model. For example, in a predictive model 124 using constituent models to predict future values of pain-relevant parameters, the model receives consistent feedback as to the accuracy of these predictions once the pain-relevant parameter is measured. This feedback can be used to adjust parameters of the model, including individualized thresholds for that user to produce categorical inputs or outputs from continuous values, or baseline values for biological rhythms associated with the patient. Alternatively, feedback can be provided from a final output of the model and compared to other data, such as a user-reported status (e.g., pain level), to provide feedback to the model. In one implementation, a reinforcement learning approach can be used to adjust the model parameters based on the accuracy of either predicted future values of pain-relevant parameters at intermediate stages of the predictive model 124 or the output of the predictive model. For example, a decision threshold used to generate a categorical output from a continuous index produced by the predictive model 124 can be set at an initial value based on feedback from a plurality of models from previous users and adjusted via the reinforcement model to generate a decision threshold specific to the user.

Figure 2:
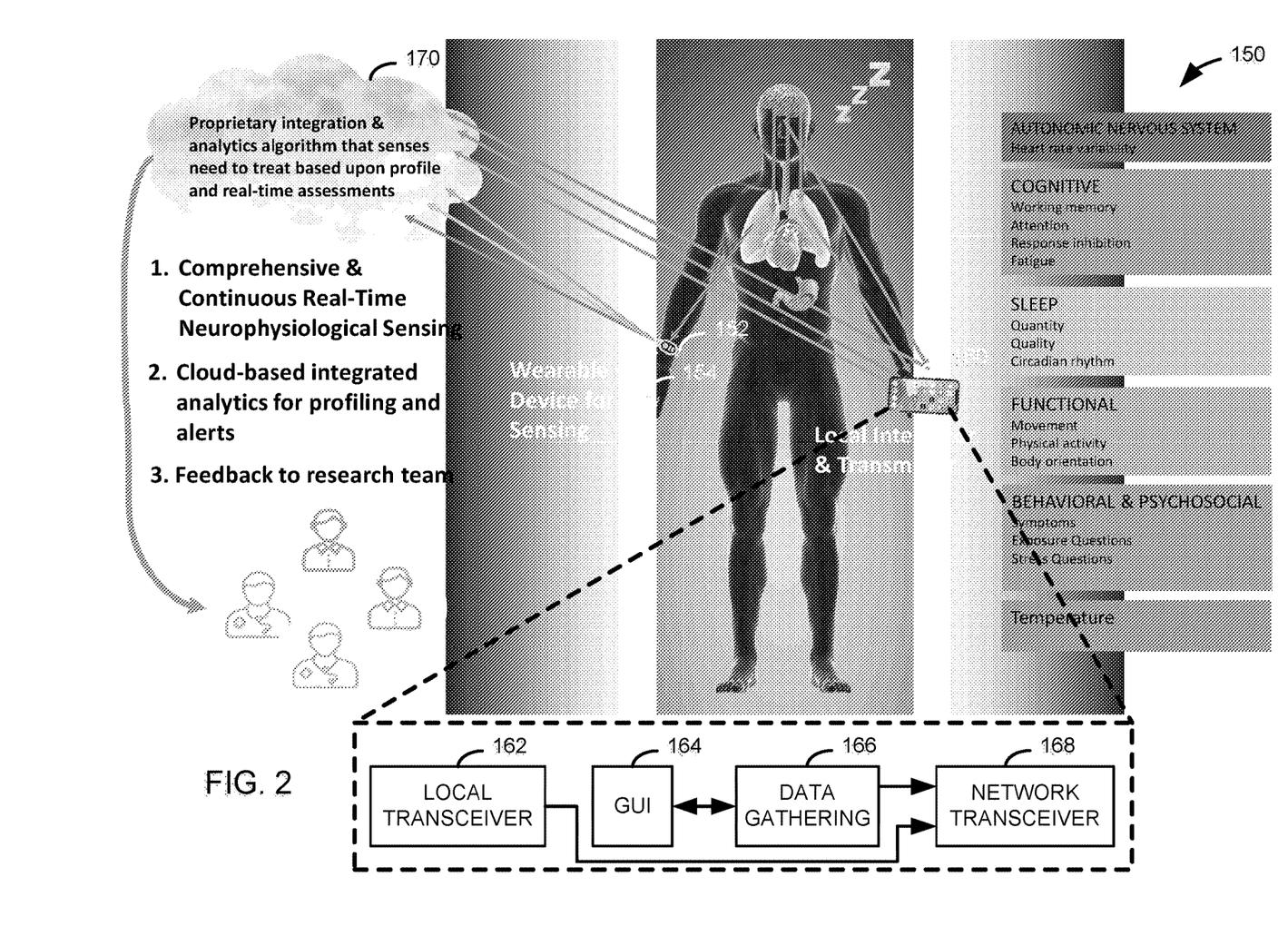
FIG. 2 is a schematic example of the system of FIG. 1 using a plurality of portable monitoring devices.
Figure 3:
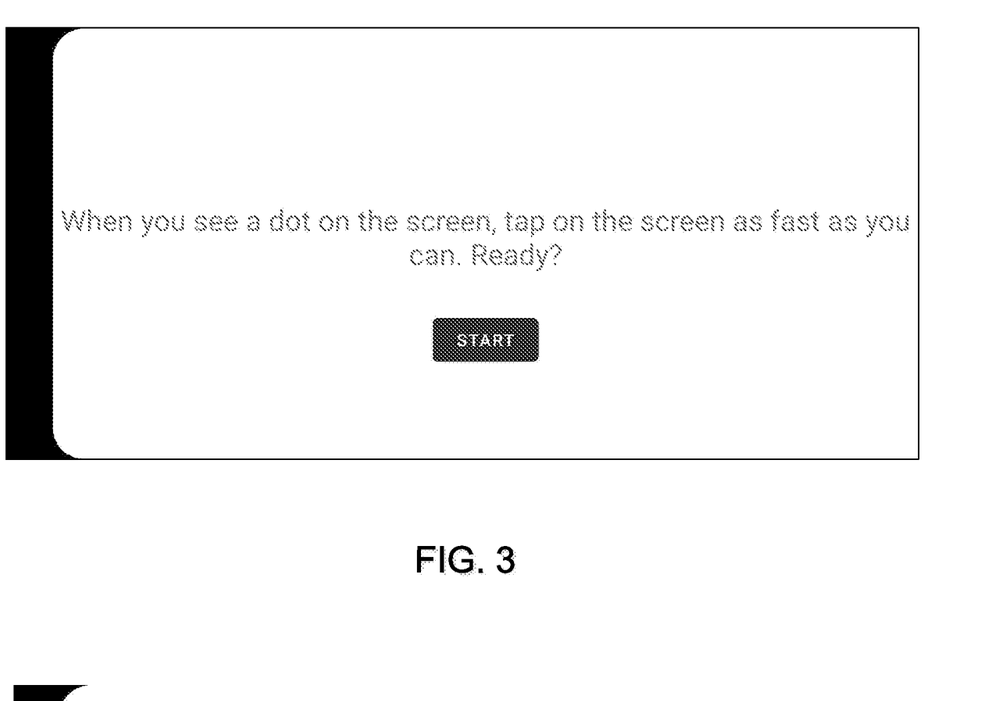
FIG. 3 is a screenshot of a reaction time test from an example cognitive assessment application.
Figure 4:
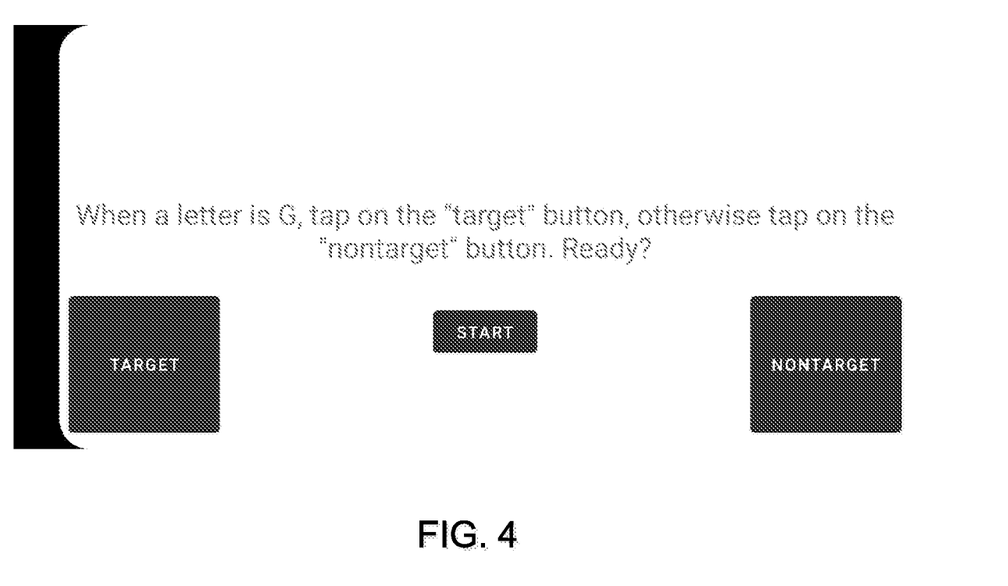
FIG. 4 is a screenshot of an attention test from an example cognitive assessment application.
Figure 5:
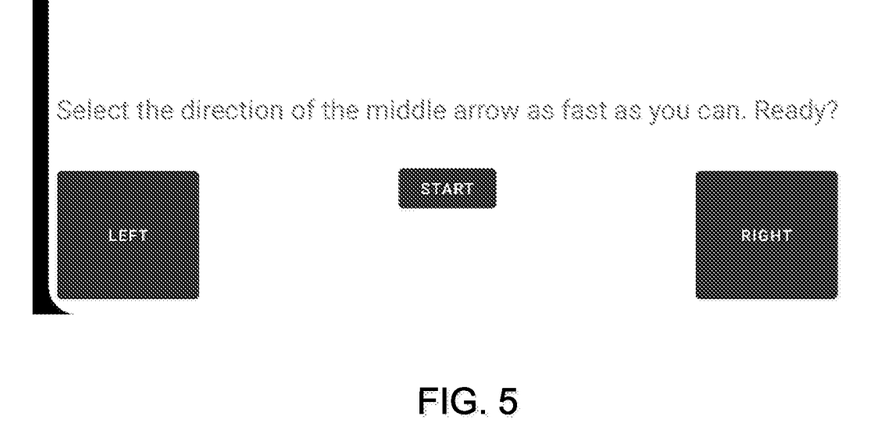
FIGS. 5 and 6 are screenshots of a response inhibition test from an example cognitive assessment application.
Figure 6:
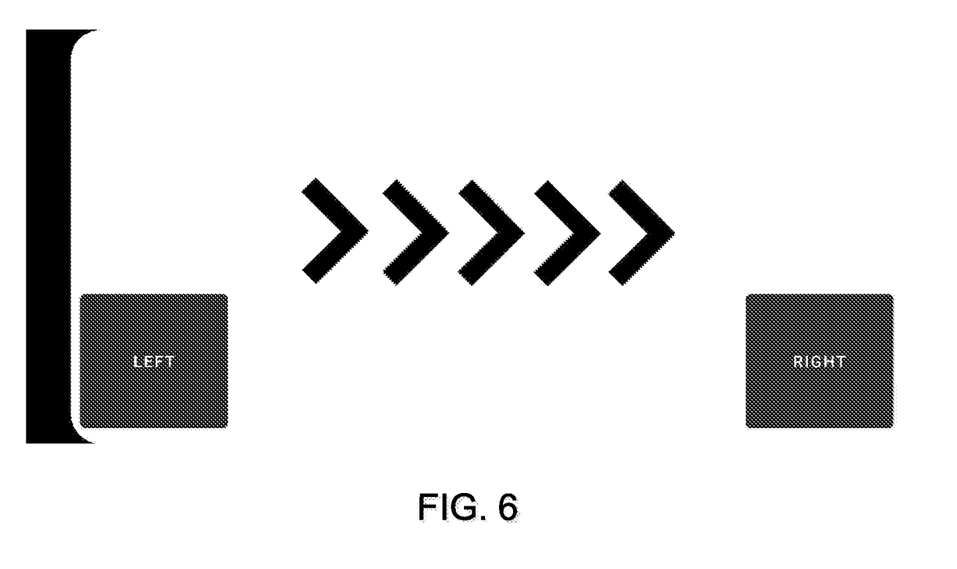
Figure 7:
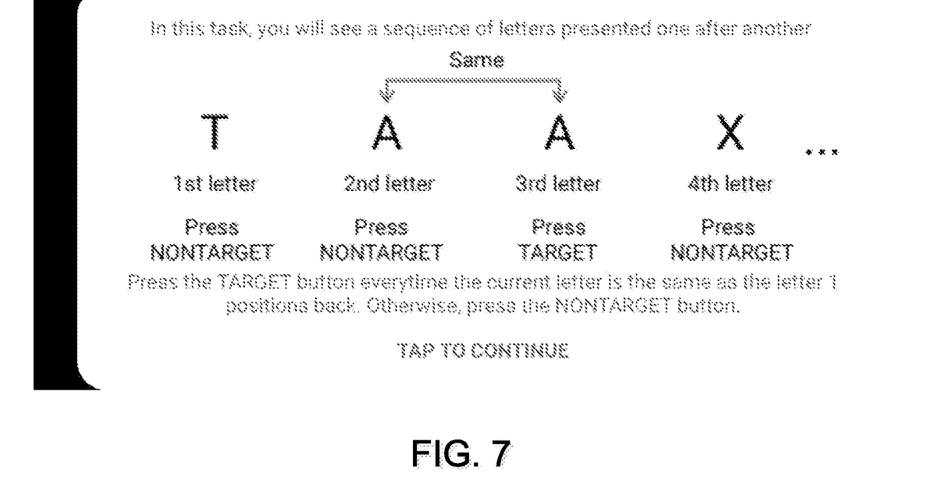
FIG. 7 is a screenshot of a working memory (1-back) test from an example cognitive assessment application.
Figure 8:
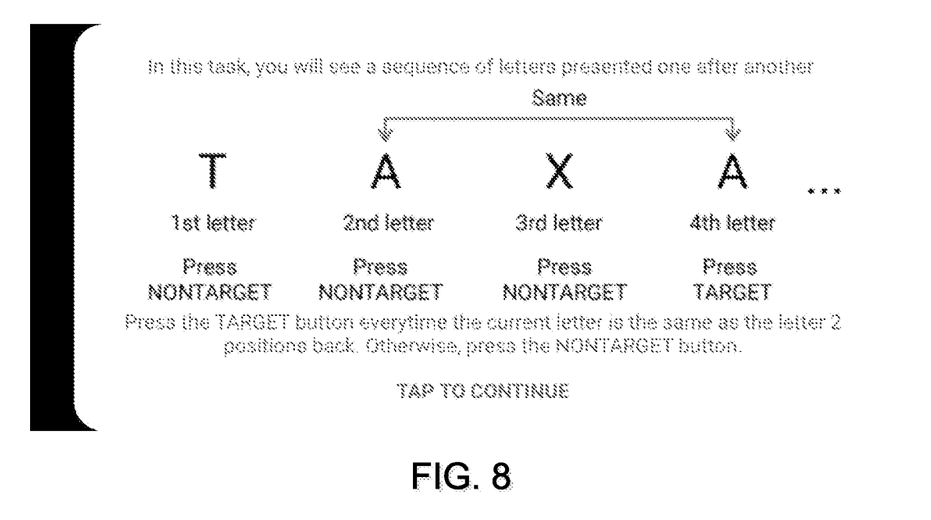
FIG. 8 is a screenshot of a working memory (2-back) test from an example cognitive assessment application.

FIG. 2 is a schematic example 150 of the system of FIG. 1 using a plurality of portable monitoring devices 152, 154, and 160. In the illustrated implementation, the first and second portable monitoring devices 152 and 154 are wearable devices, worn on the wrist and finger, respectively. Pain-relevant parameters monitored by the first and second portable monitoring devices 152 and 154 can include, for example, heart rate, heart rate variability, metrics of sleep quality, biological, and circaidian rhythm variations, metrics of sleep quantity, physical activity of the user, body orientation, movement, arterial blood pressure, respiratory rate, peripheral arterial oxyhemoglobin saturation, as measured by pulse oximetry, maximum oxygen consumption, temperature, and temperature variation. Wearable devices, as used herein, can include any wearable items implemented with appropriate sensors, including watches, wristbands, rings, headbands, headbands, and other wearable items that can maintain sensors in an appropriate position for monitoring the pain-relevant parameters. It will be appreciated that a given wearable device 152 and 154 can monitor many of these parameters with great frequency (e.g., every five minutes) allowing for a detailed time series of data to be generated.

The system 150 can further include a mobile device 160 that communicates with the first and second portable monitoring devices 152 and 154 via a local transceiver 162. The mobile device 160 can also include a graphical user interface 164 that allows a user to interact with one or more data gathering applications 166 stored at the base unit. One example of a possible data gathering applications can include a cognitive assessment application that tests various measures of cognitive function. These can include working memory, attention, and response inhibition, fatigue, cognition. Further, these metrics can be compared to an established baseline to estimate a measure of fatigue for the user. Screenshots from an example cognitive assessment application are provided as FIGS. 3-8. Another data gathering application can include a questionnaire application that allows the user to self-report pain, mood, mental, physical, and emotional states, and stress. In general, the data gathering applications 166 can be selected and configured to monitor each of:

1. Attention, alertness, and fatigue
2. Memory
3. Mental flexibility
4. Mood & Emotion
5. Perceptual processing
6. Sensory acuity
7. Motor function
8. Neuro capacity
9. Social network
10. Social systems
11. Pain rating
12. Pain location
13. Wellness
14. Alertness
15. Medical and treatment history
16. Return to work, improvement of cognitive, motor, sensory and behavioral function quality of life and function.

The mobile device 160 further comprises a network transceiver 168 via which the system 150 communicates with a remote server 170 via a local area network or Internet connection. In this example, the remote server 170 includes a predictive model implemented as a recurrent neural network, specifically a network with a long short-term memory architecture. In this example, pain-relevant parameters from the wearable devices 152 and 154, such as heart-rate variability and respiratory rate, in combination with questionnaire responses and cognitive assessment, can be provided to the predictive model as time series along with other relevant data. An output of the model is an index representing the current level of pain being experienced by the patient.

It will be appreciated that the index can be used for clinical studies to determine a response to pain treatment or responses to stimuli. Further, the index can be used to dispense medication or another therapeutic intervention to a patient for pain, either by providing the index for use by a medical professional or automatically, by actuating an infusion pump, spinal cord stimulator, or other device in response to an index meeting a threshold value.

Figure 9:
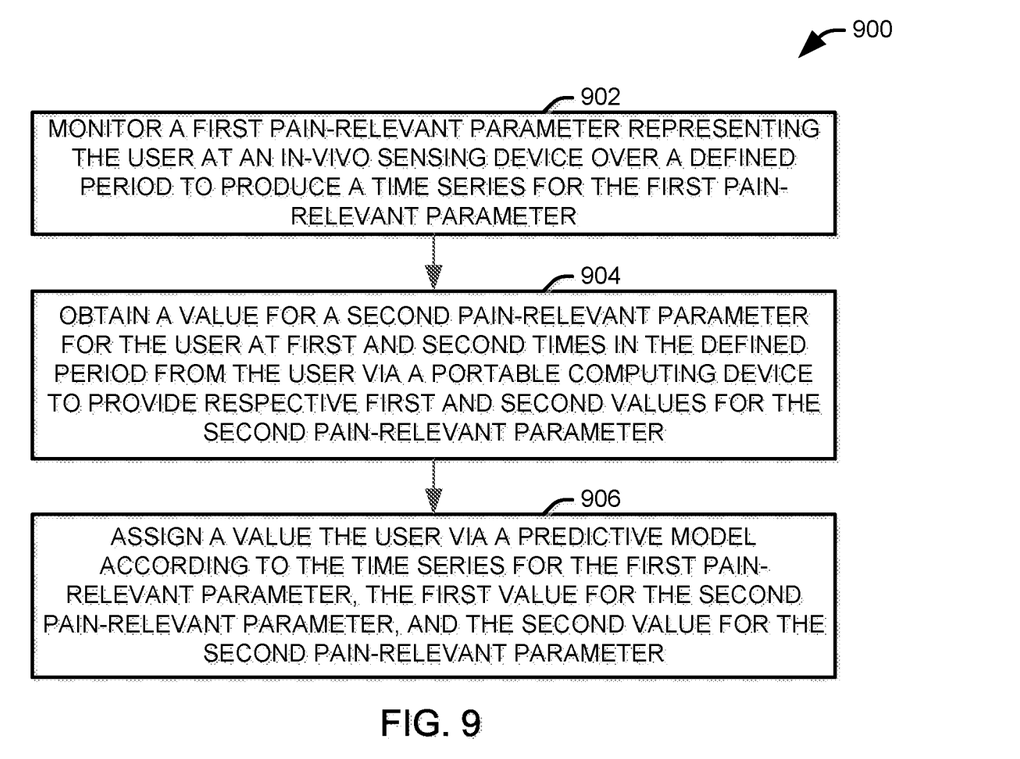
FIG. 9 illustrates a method for evaluating pain for a user.

FIG. 9 illustrates a method 180 for evaluating pain for a user. The result of the method is a value representing a current or predicted pain level of the user. At 182, a first pain-relevant parameter representing the user is monitored at an in-vivo sensing device over a defined period to produce a time series for the first pain-relevant parameter. In one example, the first pain-relevant parameter is one of a motor parameter and a physiological parameter, for example, a measure of the activity of the user, a breath rate of the user, a heart rate of the user, or a hear rate variability of the user.

At 184, a value is obtained for a second pain-relevant parameter for the user at first and second times in the defined period from the user via a portable computing device to provide respective first and second values for the second pain-relevant parameter. In one example, the second pain-relevant parameter is one of a cognitive parameter, a sleep parameter, and a psychosocial parameter determined from an input of the user at a user interface of the portable computing device, for example, a measure of attention, a measure of fatigue, a measure of sleep quality, or a metric representing a mood of the patient.

At 186, a value is assigned to the user via a predictive model according to the time series for the first pain-relevant parameter, the first value for the second pain-relevant parameter, and the second value for the second pain-relevant parameter. In one example, a wavelet decomposition is performed on the time series for the first pain-relevant parameter to provide a set of wavelet coefficients, and the set of wavelet coefficients or one or more values derived from the set of wavelet coefficients can be provided to the predictive model. Additionally or alternatively, the user can be assigned a predicted value representing a future value of the first pain-relevant parameter according to the values for the first and second pain-relevant parameters, and the value assigned to the user can be assigned based on the predicted value.

Additionally or alternatively, the user can be assigned a set of wellness values representing an overall wellness of the user from the values for the first and second pain-relevant parameters, and the value assigned to the user can be assigned based on the set of wellness values. The set of wellness values can include, for example, a first value representing fatigue, a second value representing emotional stress, a third value representing physical stress, and a fourth value representing sleep quality. In one implementation, feedback, in the form of a self-reported pain level from the user, can be used to refine the predictive model. For example, the self-reported pain level can be compared to the value assigned to the user via a predictive model, and a parameter associated with the predictive model can be changed according to the comparison. In one example, this can be accomplished by generating a reward for a reinforcement learning process based on a similarity of the measured outcome to the value assigned to the user and changing the parameter via the reinforcement learning process.

It will be appreciated that each of the wellness values and the value assigned to the user can be provided, for example, via a user interface or network interface, to one or more of the user, the user's health care provider, the user's care team, a research team, a user's workplace, or other interested entities. This allows the value to be used to make decisions about the user's care and activities including the improvement or optimization of a diagnosis of chronic pain and pain severity, pain management, decisions on return to work, performance, and function, and guiding therapies for pain including medications, lesioning, and other procedures such as neuromodulation including neurostimulation, spinal cord stimulation, infusion and other approaches. Feedback provided to the user can be used to improve the user's awareness, perception and interpretation of being in an overall positive (e.g., decreased pain) and negative (e.g., increased pain) states, allowing the user to learn strategies for avoiding negative states and inducing positive states. The provided wellness data can also be used for improvement or optimization of cognitive, motor, sensory, and behavioral function as well as generally attempting to improve the user's quality of life.

Figure 10:
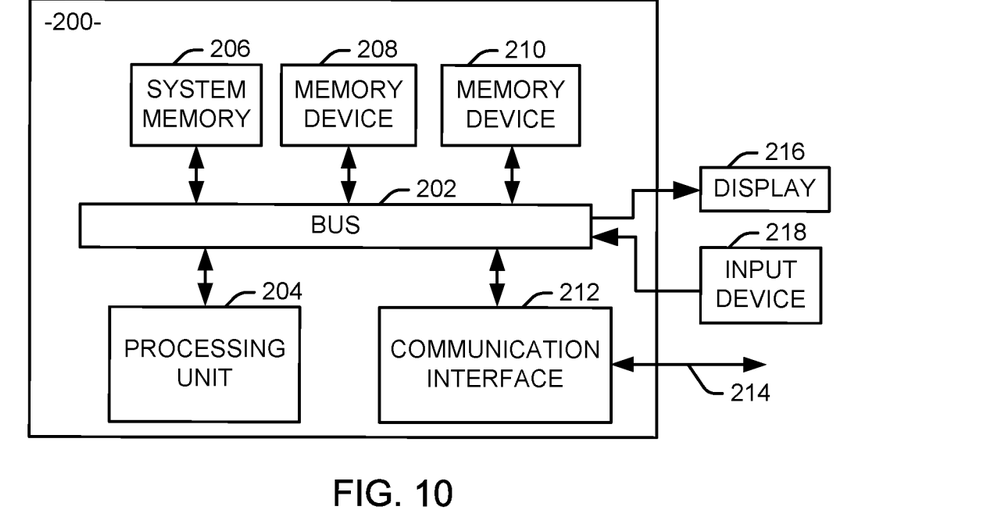
FIG. 10 is a schematic block diagram illustrating an exemplary system of hardware components.

FIG. 10 is a schematic block diagram illustrating an exemplary system 200 of hardware components capable of implementing examples of the systems and methods disclosed herein. The system 200 can include various systems and subsystems. The system 200 can be a personal computer, a laptop computer, a workstation, a computer system, an appliance, an application-specific integrated circuit (ASIC), a server, a server BladeCenter, a server farm, etc.

The system 200 can include a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard, touch screen, and/or a mouse). The system bus 202 can be in communication with the processing unit 204 and the system memory 206. The additional memory devices 208 and 210, such as a hard disk drive, server, standalone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208, and 210 can store data, programs, instructions, database queries in text or compiled form, and any other information that may be needed to operate a computer. The memories 206, 208 and 210 can be implemented as computer-readable media (integrated or removable), such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a system for evaluating the pain of a user in accordance with the present invention. Computer executable logic for implementing the system resides on one or more of the system memory 206, and the memory devices 208 and 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to, portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method for treating pain for a user, the method comprising:

monitoring a first pain-relevant parameter representing the user at an in-vivo sensing device over a defined period to produce a time series for the first pain-relevant parameter;

obtaining a value for a second pain-relevant parameter for the user at first and second times in the defined period from the user via a portable computing device to provide respective first and second values for the second pain-relevant parameter; and assigning a value to the user via a recurrent neural network according to the time series for the first pain-relevant parameter, the first value for the second pain-relevant parameter, and the second value for the second pain-relevant parameter, the value representing one of a predicted level of pain for the user at a future time and a current level of pain for the user;

receiving a self-reported pain level from the user;

changing a parameter associated with the recurrent neural network based on the self-reported pain level and the value assigned to the user via the recurrent neural network, the parameter comprising one of an individualized threshold used to produce categorical outputs for the user and a baseline value for at least one biological rhythm of the user, according to a comparison of the self-reported pain level to the value assigned to the user via the recurrent neural network; and actuating a worn or implanted therapeutic device associated with the user when the value representing the one of the predicted level of pain for the user and the current level of pain for the user exceeds the individualized threshold.

2. The method of claim 1, wherein the value represents a current level of pain experienced by the user.

3. The method of claim 1, wherein the value represents a predicted level of pain that will be experienced by the user at a future time.

4. The method of claim 1, wherein assigning a value to the user via a recurrent neural network according to the time series for the first pain-relevant parameter comprises performing a wavelet decomposition on the time series for the first pain-relevant parameter to provide a set of wavelet coefficients, and assigning the value according to at least the set of wavelet coefficients, the first value for the second pain-relevant parameter, and the second value for the second pain-relevant parameter.

5. The method of claim 1, wherein changing the parameter associated with the recurrent neural network according to the comparison of the self-reported pain level to the value assigned to the user via the recurrent neural network comprises generating a reward for a reinforcement learning process based on a similarity of the self-reported pain level to the value assigned to the user and changing the parameter via the reinforcement learning process.

6. The method of claim 1, wherein assigning the value to the user via the recurrent neural network comprises:

assigning the user a predicted value representing a future value of the first pain-relevant parameter according to the time series for the first pain-relevant parameter, the first value for the second pain-relevant parameter, and the second value for the second pain-relevant parameter; and assigning the value to the user according to at least the predicted value.

7. The method of claim 1, wherein assigning the value to the user via the recurrent neural network comprises:

assigning the user a set of wellness values, each representing an overall wellness of the user, from at least the time series for the first pain-relevant parameter, the first value for the second pain-relevant parameter, and the second value for the second pain-relevant parameter; and assigning the value to the user according to the set of wellness values.

8. The method of claim 7, wherein the set of wellness values includes a first value representing fatigue, a second value representing stress, and a third value representing sleep quality.

9. The method of claim 1, wherein the first pain-relevant parameter is one of a motor parameter and a physiological parameter.

10. The method of claim 1, further comprising providing the value assigned to the user to one of a health care provider, a care team, a research team, and a workplace of the user via a network interface.

11. The method of claim 1, wherein the second pain-relevant parameter is one of a cognitive parameter, a sleep parameter, and a psychosocial parameter.

12. The method of claim 11, wherein the second pain-relevant parameter is a metric representing a sleep quality of the user.

13. The method of claim 1, wherein actuating the worn or implanted therapeutic device associated with the user comprises actuating a worn or implanted device that provides neuromodulation to the user.

14. A system for treating pain for a user, the system comprising:
   an in-vivo sensing device that monitors a first pain-relevant parameter representing the user over a defined period to produce a time series for the first pain-relevant parameter;
   a portable computing device obtaining a value for a second pain-relevant parameter for the user at first and second times in the defined period to provide respective first and second values for the second pain-relevant parameter;
   a recurrent neural network that assigns a value to the user according to the time series for the first pain-relevant parameter, the first value for the second pain-relevant parameter, and the second value for the second pain-relevant parameter, the value representing a predicted level of pain for the user at a future time; and
   a feedback component that receives a self-reported pain level from the user, compares the self-reported pain level to the value assigned to the user via the recurrent neural network, and changes a parameter associated with the recurrent neural network according to the comparison of the measured outcome to the value assigned to the user via the recurrent neural network, the parameter comprising one of an individualized threshold used to produce categorical outputs for the user and a baseline value for at least one biological rhythm of the user; and
   a worn or implanted therapeutic device associated with the user that is actuated when the value representing the predicted level of pain for the user exceeds the individualized threshold.

15. The system of claim 14, wherein the second pain-relevant parameter is derived from psychosocial assessment data provided by the user, the portable computing device comprising a user interface that allows the user to interact with a psychosocial assessment application.

16. The system of claim 15, wherein the second pain-relevant parameter represents a level of stress experienced by the user.

17. The system of claim 14, wherein the in-vivo sensing device is a wearable device that tracks activity of the user, and the first pain relevant parameter is a motor parameter representing a deviation of the user from an established pattern of activity.

18. The system of claim 14, wherein the user is provided with messages on the portable computing device to which the user can respond via a user interface, the second pain-relevant parameter representing a level of compliance of the user in responding to the provided messages.

19. The system of claim 14, wherein the worn or implanted therapeutic device is a drug infusion pump.

20. A system for treating pain for a user, the system comprising:
   a wearable device that monitors a first pain-relevant parameter representing the user over a defined period to produce a time series for the first pain-relevant parameter, the first pain-relevant parameter being one of a motor parameter and a physiological parameter;
   a portable computing device obtaining a value for a second pain-relevant parameter for the user at first and second times in the defined period to provide respective first and second values for the second pain-relevant parameter, the second pain-relevant parameter being one of a cognitive parameter, a sleep parameter, and a psychosocial parameter determined from an input of the user via a user interface of the portable computing device;
   a recurrent neural network that assigns a value to the user according to the time series for the first pain-relevant parameter, the first value for the second pain-relevant parameter, and the second value for the second pain-relevant parameter, the value representing a current level of pain for the user;
   a feedback component that receives a self-reported pain level from the user, compares the self-reported pain level to the value assigned to the user via the recurrent neural network, and changes a parameter associated with the recurrent neural network via a reinforcement learning process according to the comparison of the measured outcome to the value assigned to the user via the recurrent neural network, the parameter comprising one of an individualized threshold used to produce categorical outputs for the user and a baseline value for at least one biological rhythm of the user; and
   a worn or implanted therapeutic device associated with the user that is actuated when the value representing the predicted level of pain for the user exceeds the individualized threshold.

* * * * *